United States Patent
Colleran et al.

(10) Patent No.: US 7,776,051 B2
(45) Date of Patent: Aug. 17, 2010

(54) SYSTEM AND METHOD FOR DISPLACEMENT OF BONY STRUCTURES

(75) Inventors: Dennis Colleran, Frisco, TX (US); Jennifer Diederich, Arlington, TX (US)

(73) Assignee: Theken Spine, LLC, Akron, OH (US)

( * ) Notice: Subject to any disclaimer, the term of this patent is extended or adjusted under 35 U.S.C. 154(b) by 1689 days.

(21) Appl. No.: 10/837,724

(22) Filed: May 3, 2004

(65) Prior Publication Data
US 2005/0245928 A1 Nov. 3, 2005

(51) Int. Cl.
*A61B 17/58* (2006.01)
(52) U.S. Cl. ..................................... 606/105
(58) Field of Classification Search ............... 606/61, 606/104, 105, 279, 246, 86 A
See application file for complete search history.

(56) References Cited

U.S. PATENT DOCUMENTS

| | | | |
|---|---|---|---|
| 4,025,053 A | 5/1977 | Stickle, Jr. | |
| 4,827,918 A | 5/1989 | Olerud | |
| 4,926,849 A | 5/1990 | Downey | |
| 5,163,940 A * | 11/1992 | Bourque | 606/96 |
| 5,167,662 A | 12/1992 | Hayes et al. | |
| 5,297,538 A | 3/1994 | Daniel | |
| 5,395,303 A | 3/1995 | Bonutti et al. | |
| 5,439,463 A | 8/1995 | Lin | |
| 5,443,515 A | 8/1995 | Cohen et al. | |
| 5,466,237 A | 11/1995 | Byrd, III et al. | |
| 5,474,555 A | 12/1995 | Puno et al. | |
| 5,540,687 A | 7/1996 | Fairley et al. | |
| 5,700,263 A | 12/1997 | Schendel | |
| 6,090,113 A | 7/2000 | Le Couedic et al. | |
| 6,126,660 A | 10/2000 | Dietz | |
| 6,340,363 B1 | 1/2002 | Bolger et al. | |
| 6,530,929 B1 | 3/2003 | Justis et al. | |
| 6,551,316 B1 | 4/2003 | Rinner et al. | |
| 6,716,218 B2 | 4/2004 | Holmes et al. | |
| 6,749,613 B1 | 6/2004 | Conchy | |
| 6,802,844 B2 | 10/2004 | Ferree | |
| 6,837,889 B2 | 1/2005 | Shluzas | |
| 7,008,422 B2 * | 3/2006 | Foley et al. | 606/61 |

(Continued)

FOREIGN PATENT DOCUMENTS

EP 0 159 007 10/1985

(Continued)

OTHER PUBLICATIONS

International Search Report and Written Opinion issued for PCT/US2005/015521 dated Dec. 12, 2005.

*Primary Examiner*—Thomas C Barrett
*Assistant Examiner*—Michael J Araj
(74) *Attorney, Agent, or Firm*—Middleton Reutlinger; Robert H. Eichenberger; Chad D. Bruggeman

(57) ABSTRACT

Systems and methods for displacing bony structures relative to each other using a single device is disclosed. Displacement includes distraction and compression. Bony structures are engaged with displacement arms. The user selects one of a plurality of manners in which to manipulate a user interface, where a first manner results in compression and a second manner results in distraction. The user interface is manipulated in the selected manner until a desired amount of displacement has been reached. This displacement is performed in a manner that is minimally invasive to the patient.

28 Claims, 8 Drawing Sheets

U.S. PATENT DOCUMENTS

| | | |
|---|---|---|
| 7,008,432 B2 | 3/2006 | Schläpfer et al. |
| 7,011,658 B2 | 3/2006 | Young |
| 7,160,300 B2 * | 1/2007 | Jackson ............ 606/61 |
| 7,188,626 B2 * | 3/2007 | Foley et al. ............ 128/898 |
| 2002/0123754 A1 * | 9/2002 | Holmes et al. ............ 606/105 |
| 2003/0153911 A1 | 8/2003 | Shluzas |
| 2004/0143265 A1 | 7/2004 | Landry et al. |
| 2004/0176766 A1 | 9/2004 | Shluzas |
| 2004/0267279 A1 | 12/2004 | Casutt et al. |
| 2005/0070917 A1 | 3/2005 | Justis |
| 2005/0080418 A1 | 4/2005 | Simonson et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0277919 A1 | 12/2005 | Slivka et al. |
| 2006/0009777 A1 | 1/2006 | Lim |
| 2006/0149252 A1 | 7/2006 | Markworth et al. |

FOREIGN PATENT DOCUMENTS

| | | |
|---|---|---|
| WO | WO 2004/047650 | 6/2004 |
| WO | WO2005120401 | 12/2005 |
| WO | WO2005122926 | 12/2005 |

* cited by examiner

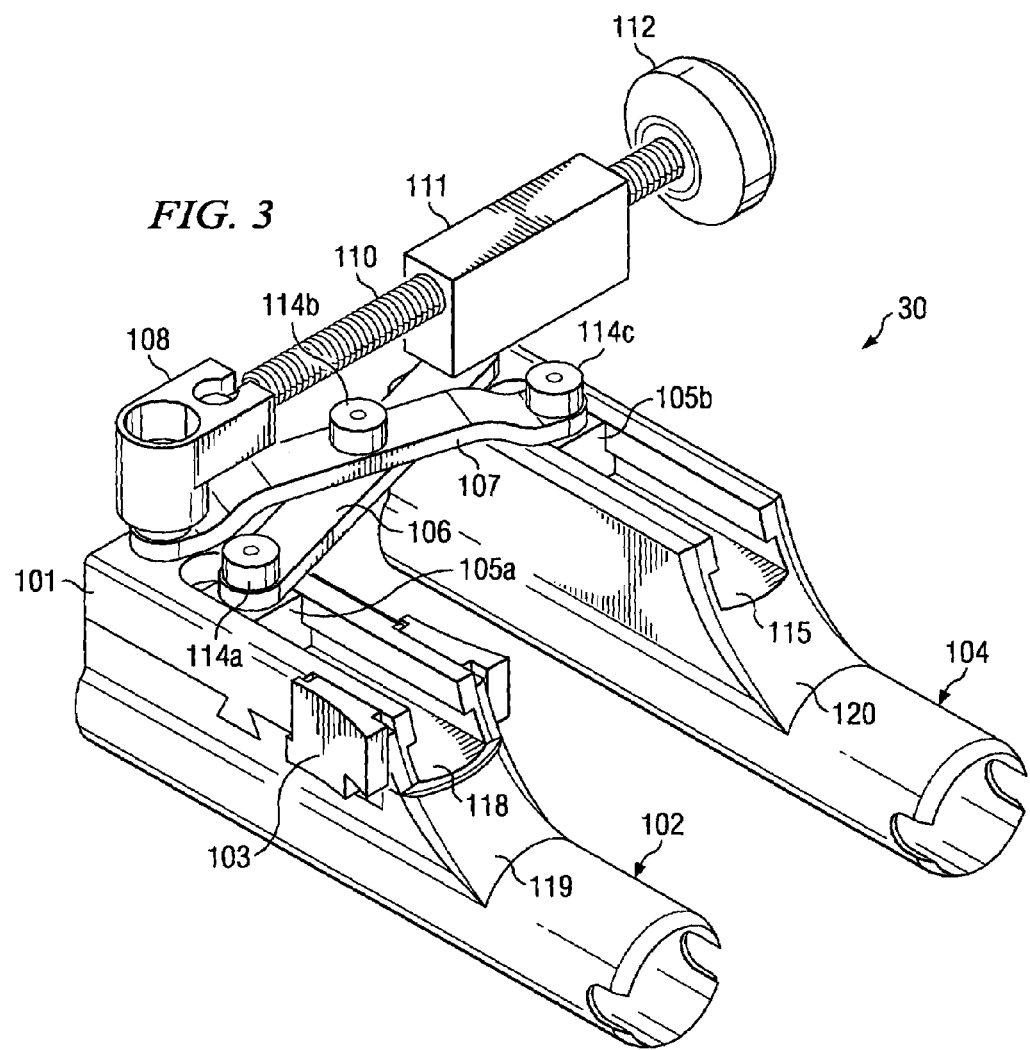

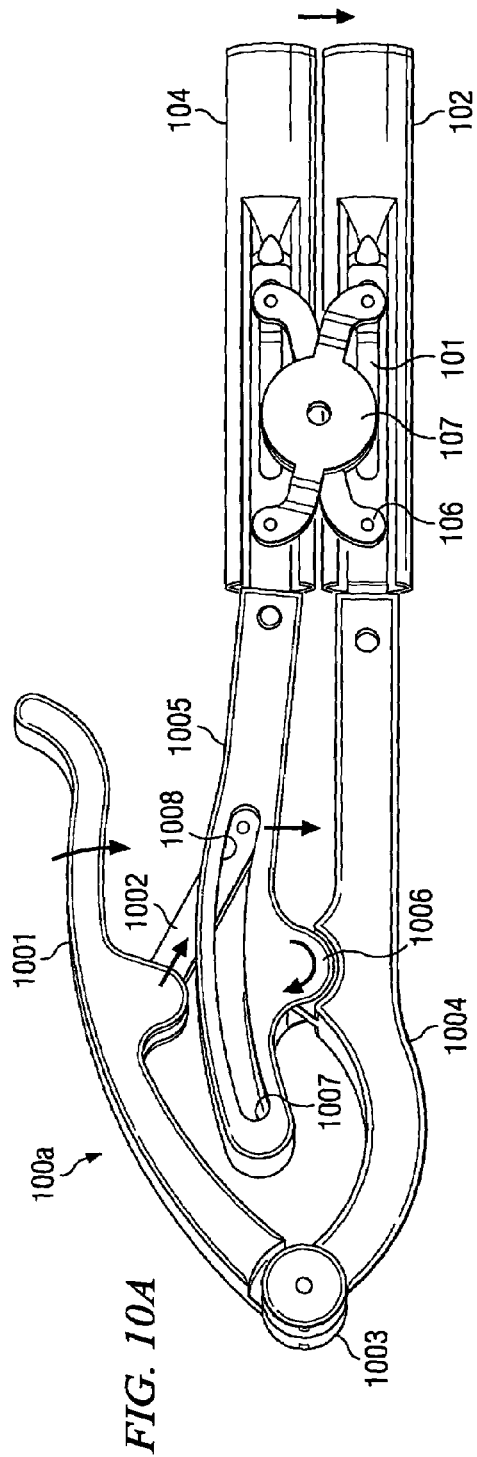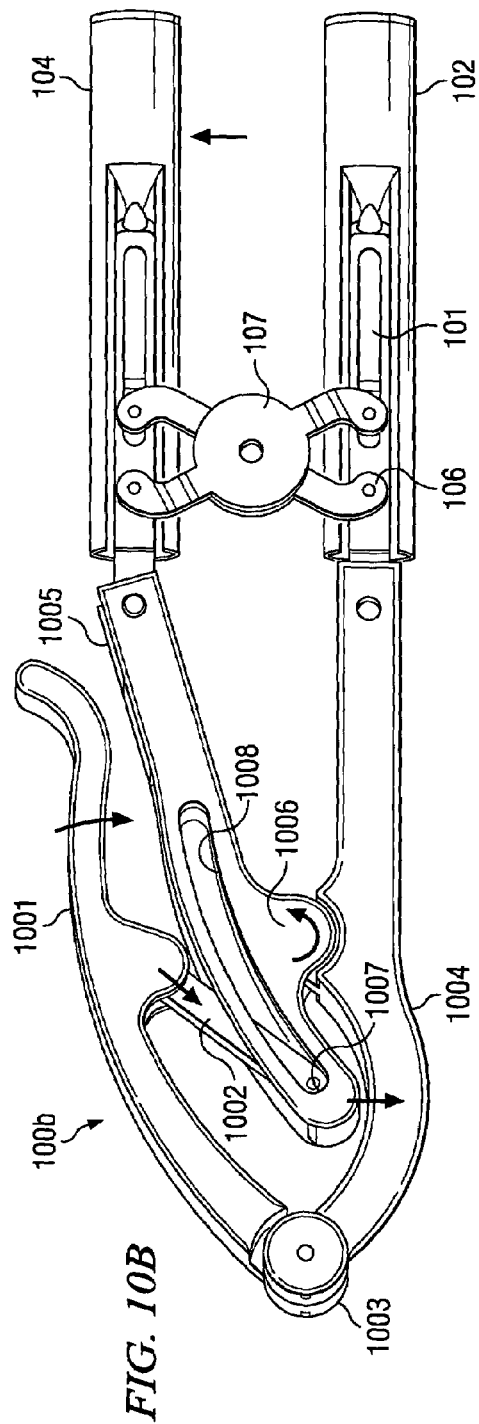
FIG. 10A
FIG. 10B

SYSTEM AND METHOD FOR DISPLACEMENT OF BONY STRUCTURES

CROSS-REFERENCE TO RELATED APPLICATIONS

This application relates to co-pending and commonly assigned U.S. patent application Ser. No. 10/690,211, filed Oct. 21, 2003, entitled "SYSTEM AND METHOD FOR STABILIZING OF INTERNAL STRUCTURES", the disclosure of which is hereby incorporated herein by reference.

TECHNICAL FIELD

The present invention relates generally to the medical field, and more particularly to a system and method for displacing bony structures relative to each other.

BACKGROUND OF THE INVENTION

When a patient suffers from orthopedic injuries, deformities or degenerative diseases, it is sometimes necessary to insert implants into the patient's body to stabilize an internal structure, promote healing, or relieve pain. In the area of spinal surgery, for example, a common procedure involves the use of screws or hooks joined by a connecting brace in order to secure bones. Once the brace is placed in the patient's body, the brace must be firmly secured to the screws or hooks in order to provide a stable construct which effectively immobilizes a corresponding portion of the spine. Then, a set screw or locking element presses against the brace to secure the brace to the hooks or screws.

When surgery is performed, the surgeon often needs to distract bone by pulling it away from the work site or compress bone to pull it together if broken, as an example. In the area of spinal surgery, a surgeon may approach the spinal column of a patient from a posterior position, and force is applied in order to move implants along a rod in order to distract or compress bone or implants into the most favorable position. Force also may be applied to distract or compress prior to insertion of a rod.

In the past, two separate devices have been used to perform compression and distraction. As an example, U.S. Pat. No. 6,716,218 issued to Holmes et al., teaches a device that performs distraction. If the surgeon desires to perform compression, another device would be required. Additionally, this type of compression or distraction device is not minimally invasive. Rather, a large incision is required to use this device. Thus, during a procedure, a surgeon has to switch devices depending on whether compression or distraction is desired. This need for switching devices may increase the amount of time required to perform the procedure, and thus may result in a longer recovery time for the patient.

Alternatively, certain devices are available that allow for parts to be substituted, or changed out, in order to perform distraction or compression. As shown in U.S. Pat. No. 6,551,316. ("the '316 patent"), for example, a device is provided having two sets of handles that can be selectively interconnected on an assembly. One set of handles would be affixed to a jaw section when compression is needed. This first set of handles may be substituted with the second set of handles configured to be used for distraction as desired. If the surgeon desires to perform compression, one set of handles is attached to the assembly, and if distraction is desired, then the set of handles for compression must be removed and replaced with the set of handles for use in distraction. Accordingly, it takes time for the surgeon to replace the handles during the procedure. Further, the surgeon must remove the jaw section of the device from the patient's body if he/she decides to employ a different technique, causing the length of the surgical procedure to increase. Additionally, the handles of the device described in the '316 patent that the surgeon manipulates are relatively large, causing the device to be top-heavy due to the size of the handles. The surgeon's hand would likely cover approximately half to two-thirds of the handle portion in order to steady the device during the procedure. Thus, the device cannot be left unattended inside the patient. Also, the device of the '316 patent is not minimally invasive, but instead requires a large incision to insert the jaws of the device. Even if the surgical procedure itself is minimally invasive, use of the non-minimally invasive '316 patent device would effectively block the surgeon's ability to visualize the operative site and to conduct the operation in a minimally invasive fashion.

BRIEF SUMMARY OF THE INVENTION

In view of the above, there exists a need in the industry for a system and method for displacing, such as by compression or distraction, bony structures using a single device. Further, a need exists for a system and method for performing at least one of compression and distraction in a way that is minimally invasive (e.g., by making a smaller incision to the patient).

The present invention is directed to a system and method which allow for the displacement of bony structures, such as vertebrae of the spine relative to each other. Displacement may include at least one of compression and distraction, and embodiments of the present invention provide for a device that may perform compression and distraction interchangeably without the need for having separate compression and distraction devices. That is, embodiments of the present invention provide for an integrated device that allows for compression and distraction to be selectively performed with a single device. Further, embodiments are provided that allow for distraction and/or compression to be performed in a manner that is minimally invasive for the patient. That is, a displacement device is provided that minimizes the incision made on a patient in order to perform displacement (compression and/or distraction) of bony structures.

In certain embodiments, a medical instrument is provided that can perform both compression and distraction of vertebral bodies through at least two percutaneous incisions. This instrument allows for either distraction or compression to be selectively performed without the removal or addition of parts to the instrument. Further, no substitution of the instrument is needed to perform distraction or compression.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 3 shows an isometric view from the back of the assembled displacement device of FIG. 2;

FIG. 10A shows another example embodiment of a displacement device having a different user interface than the example device of FIGS. 1-4, wherein the user interface is configured for compression;

FIG. 10B shows the example displacement device of FIG. 10A where the user interface is configured for distraction.

DETAILED DESCRIPTION OF THE INVENTION

Figure 1:
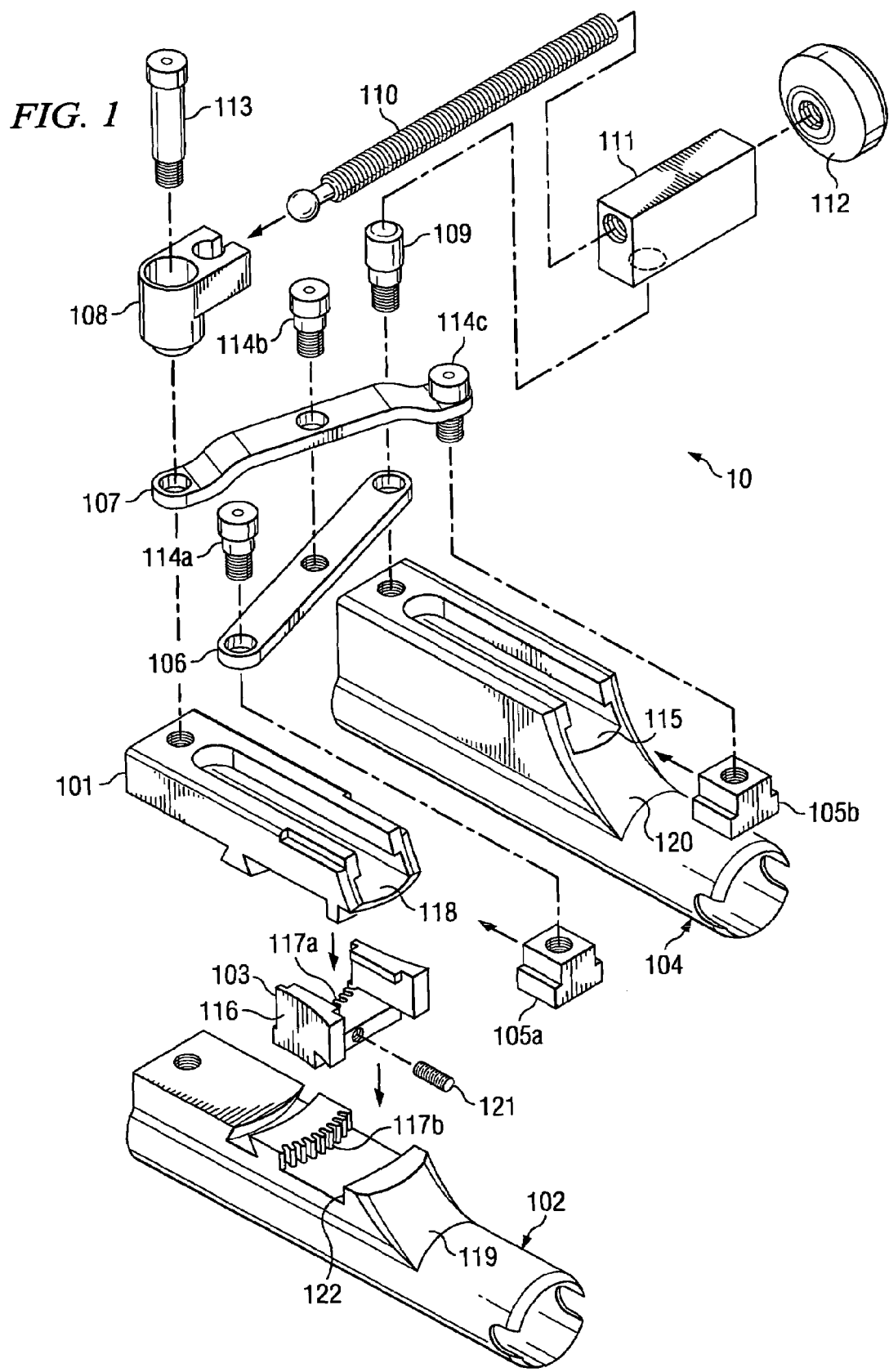
FIG. 1 shows an exploded view of an example embodiment of a displacement device.

Certain embodiments of the present invention provide a system and method which allow for both the compression and distraction of bony structures, such as a spine, during a surgical procedure. According to certain embodiments, a displacement device comprises at least two guide members connected by cross members wherein the guide members are displaced relative to each other responsive to manipulation of a user interface. The guide members provide for the transmission of distraction or compression force percutaneously to bony structures, thus allowing compression or distraction of these bony structures. Although various embodiments are described with reference to a displacement device that compresses or distracts, certain embodiments provide for a displacement device that performs at least one of compression and distraction without the need for a large incision, thereby performing compression or distraction in a minimally invasive manner.

According to certain embodiments, it is unnecessary to disassemble or change parts on the displacement device in order to compress or distract. Thus, no assembly or disassembly of the displacement device is needed during the procedure, and it is not necessary to remove the device from the patient's body if the surgeon desires to switch between compression and distraction. The displacement device is light enough, and small enough, to be left affixed to the extensions without holding. Thus, the device is sufficiently stable so as to not be removed if the surgeon ceases using it momentarily. Further, because of the size of the displacement device, the device will not interfere with the surgeon's activities during an operation. As certain embodiments provide for a displacement device that is minimally invasive, accordingly the region of the patient's body in which the surgeon is operating does not need to be fully exposed in order to perform compression or distraction. This results in minimal trauma to the patient and perhaps a faster recovery time.

Embodiments of this displacement device may be used in certain procedures in conjunction with an implantable stabilization device for maintaining the relative displacement of the bony structures acquired using the displacement device. As an example, a stabilization device may include a brace connected between anchors (e.g., pedicle screws) that anchor to the displaced bony structures. The displacement device is used in order to ensure correct positioning of the brace-screw assembly and the implant device overall preferably before an implant device is stabilized. In certain procedures, the displacement device may be used before the brace of the implanted stabilization device is locked down to stabilize displaced bony structures.

Embodiments of this displacement device may also be used in certain procedures in conjunction with an implantable dynamic stabilization device. Some dynamic stabilization devices have a need to distract elements of the spine to insert the dynamic stabilization implant and then compress those elements to complete the assembly process. This device allows for the minimally invasive distraction of that dynamic stabilization device and aid in its insertion.

FIG. 1 shows an exploded view of one example embodiment of a displacement device. Displacement device 10 is a device used to perform displacement of bony structures, such as vertebrae of the spine, relative to each other. The device 10 has two general elements: a user interface and a displacement mechanism. The displacement mechanism includes cross-action members 106, 107 and at least two guide tubes 102, 104. Each of these elements are shown in FIG. 1 and will be discussed in turn.

The user interface, as shown in the example embodiment of FIG. 1, includes knob 112 and threaded rod 110. Threaded rod coupling 108 is a receiving part for receiving the distal end of threaded rod 110. Threaded block 111 provides a movable element threadably engaged to threaded rod 110 and movable along the longitudinal axis of the rod 110 relative to receiving part 108 in response to rotation of knob 112. Shoulder screw 113 fastens threaded rod coupling 108 to the displacement mechanism. Knob 112 is affixed to threaded rod 110 wherein knob 112 can be rotated in order to displace bony structures relative to each other, as described further below.

As will be discussed further below, alternative embodiments may include a handle-based user interface rather than a threaded rod-based user interface (as will be discussed in conjunction with FIGS. 10a and 10b).

Moving to the displacement mechanism of the displacement device 10, there is shown cross-action members 106, 107 for translating received input from the user interface into relative displacement of guides 102, 104 Cross-action members 106 and 107 are coupled together via head shoulder screw 114b. Screw 114a connects member 106 to slider element 105a which is inserted in channel 118 of engaging element 101, and similarly, screw 114c connects member 107 to slider element 105b which is inserted into channel 115 of guide tube 104. As knob 112 is turned, cross-action members 106 and 107 then move relative to one another to ensure that guide tubes 102 and 104 perform compression and/or distraction as desired.

Also, below the user interface, there is shown pin 109 that mates the hole in cross-action member 106 to guide 104. Pin 109 and the holes on the underside of threaded block 111 function together as a macro adjustment for initial placement of the device.

Moving to the guide tubes of device 10, two guide tubes 102 and 104 (also referred to as "displacement arms") are shown in FIG. 1. Guide tube 102 is mated with engaging element 101 to form an adjustable guide tube. Guide tube 102 and engaging element 101 are movable relative to each other thereby allowing guide 102 to be angled relative to guide tube 104 so as not to be parallel with guide tube 104. Guide tube 104 may be referred to as "stationary" where guide tube 102 moves relative to it during displacement. Of course, movement of either or both guides may be performed to achieve the relative displacement desired.

As shown in FIG. 1, displacement device 10 includes thumb slide 103 positioned relative to guide tube 102. As will be discussed in more detail with respect to FIG. 4, thumb slide 103 is positioned on guide tube 102 and teeth 117A engage teeth 117B of guide tube 102. When a user moves thumb slide 103 downward (by engaging surface 116) to disengage teeth 117A and 117B, angulation of the guide tube 102 may be changed. When the desired level of angulation is achieved, thumb slide 103 is released upward and the teeth engage locking guide tube 102 at the particular angle. Spring 121 is arranged between wall 122 and thumb slide 103 to apply force to cause teeth 117A of thumb slide 103 to engage teeth 117B of guide 102. When sufficient force is applied to thumb slide 103, spring 121 compresses enabling teeth 117A to disengage teeth 117B.

Further, engaging element 101 and guide tube 104 of device 10 receive slider elements 105a, 105b through channels 118 and 115 respectively. As the user interface is manipulated for compression or distraction, slider elements 105a, 105b adjust up and down their respective channels to provide the desired amount of movement in the cross-members 106 and 107. As shown, there is a gradual sloping 119, 120 on the surface of guide tubes 102 and 104 respectively to allow for gentle insertion through an incision and/or movement of the guide tubes within an incision, thus reducing harm to the patient during the procedure. Displacement device 10 also provides for sloping of the leading edges of guide tubes 102 and 104 to allow a surgeon to insert guides tubes 102, 104 along extensions into a patient's body in a minimally invasive manner.

Figure 2:
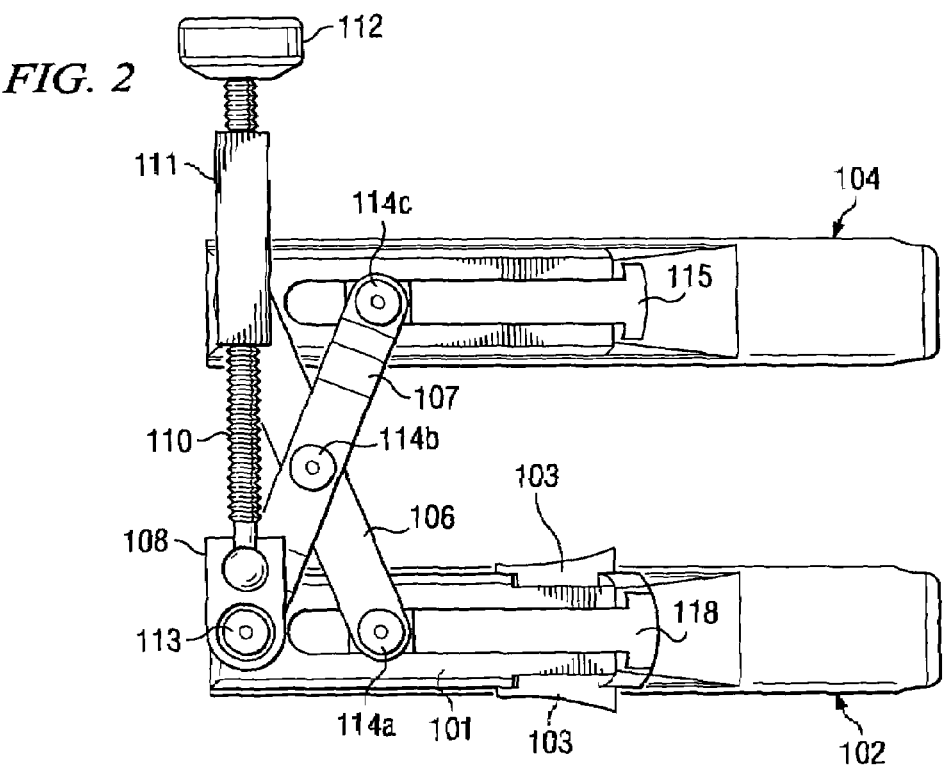
FIG. 2 shows a front view of the example displacement device of FIG. 1 when assembled.

FIG. 2 is a front view of the embodiment of FIG. 1 when assembled. As shown, the two general elements (user interface and displacement mechanism) of the displacement device are displayed. In this example embodiment, a left-hand thread is used for threaded rod 110 of the user interface. Accordingly, when knob 112 is turned to the right (clockwise), the knob will loosen and the distance between knob 112 and threaded block 111 will increase. Responsive to this action, the displacement device will compress or tighten the bony structures. Thus, guide tubes 102 and 104 will be moved closer together resulting in compression. On the other hand, if knob 112 is rotated to the left (counter-clockwise), the device will distract or loosen the bony structures relative to each other. That is, guides 102 and 104 will be pushed apart. This implementation may be desirable in that one typically thinks of turning a screw to the right (clockwise) to tighten (or compress) and turning the screw to the left (counter-clockwise) to loosen (or distract). Of course, in other implementations, a right-hand threaded screw may be used for rod 110 in which turning knob 112 clockwise results in distraction and turning knob 112 counter-clockwise results in compression.

FIG. 3 shows an isometric view of the example embodiment of FIG. 2 from the back. In FIG. 3, thumb slide 103 can be seen. Further, the sloped portions 119, 120 on the surface of guide tubes 102, 104, along with the channels 118, 115 for receiving slider elements 105a and 105b, respectively, can be seen.

Figure 4:
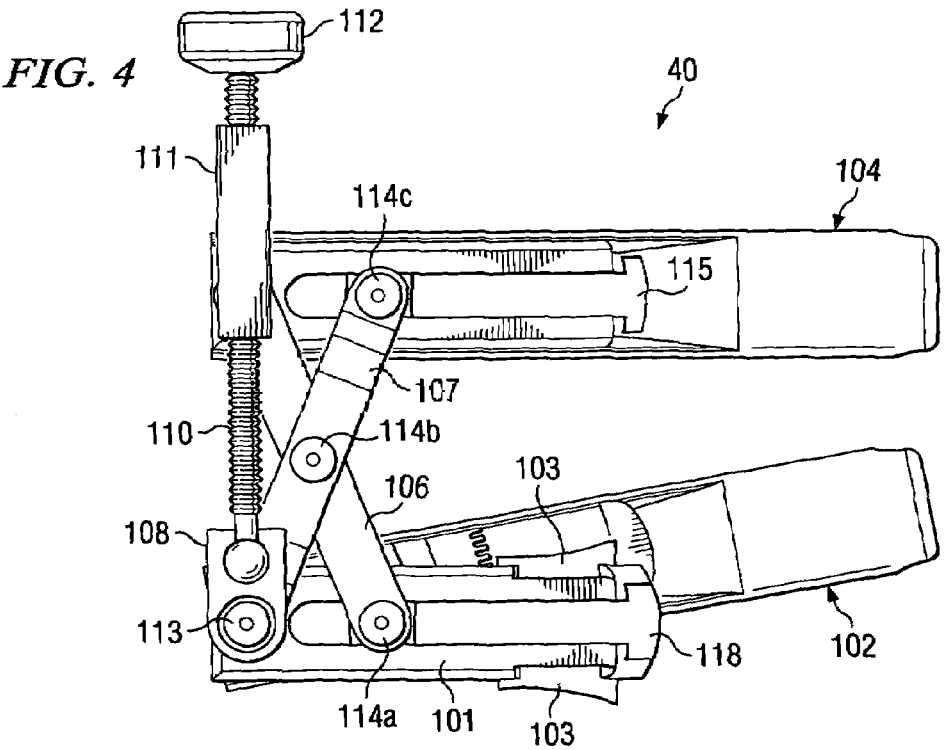
FIG. 4 shows a front view of the example assembled displacement device of FIG. 2 where one of its guides is angled so as to not be parallel with the other of its guides.

FIG. 4 illustrates a front view of the example embodiment of a displacement device 10 of FIG. 2, wherein guide tube 102 has been angularly adjusted. Thumb slide 103 is used to alter the angular positioning of guide tube 102. As shown in FIG. 4, thumb slide 103 is positioned on guide tube 102 relative to guide tube 104 so as to not be parallel with guide tube 104. Angular displacement of guide tube 102 is achieved by moving thumb slide 103 to disengage the teeth 117. Teeth 117A of thumb slide 103 engage teeth 117B. When the thumb slide shifts downward, for example, the teeth are disengaged and the angulation of guide tube 102 may be changed. While the teeth are disengaged, guide tube 102 can be adjusted until the desired angulation is achieved. Responsive, slider elements 105a and 105b slide downward in channels 118, 115 (in the direction away from rod 110), thus permitting the lower ends 106A, 107A of cross-members 106 and 107 to compress toward each other. This compression is translated to guides 102 and 104, which in turn translate the compression force to anchors (e.g., screws 602 and 603 of FIG. 6) to which the guides engage. Once guide tube 102 has been adjusted to its desired position relative to engaging element 101 to which slide 105a is slidably engaged, thumb slide 103 is released, and the teeth 117A, 117B will lock guide tube 102 into place. Similarly, when distraction is desired, slider elements 105a and 105b slide upward in channels 118, 115 (in the direction toward rod 110), thus permitting the lower ends (106A, 107A) of cross members 106 and 107 to distract away from each other. This distraction is translated to guides 102 and 104, which in turn translate distraction force to the anchors to which the guides engage.

This angular adjustment may be desired, for example, when the positioning of the anchors are not arranged perfectly parallel to each other. Further, adjustment may be desired when a connecting brace positioned between the anchors is not entirely straight (e.g., is curved to match the curvature of the patient's spine).

Figure 5:
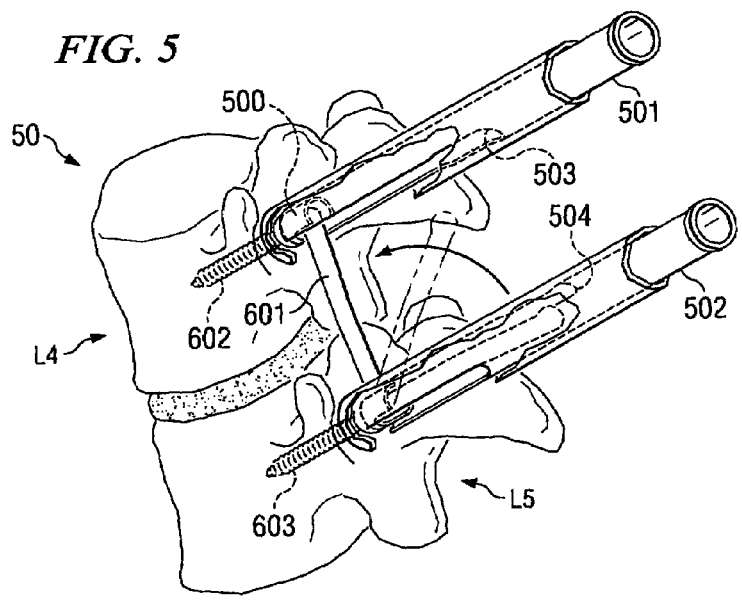
FIG. 5 shows a cut-away view illustrating a stage of installation of an example stabilization device with which embodiments of the displacement device may be used in certain procedures.

FIG. 5 shows a cut-away view illustrating a stage of installation of an example stabilization device 50 with which embodiments of the displacement device of FIGS. 1-4 may be used in certain procedures. More specifically, FIG. 5 shows a spine stabilization brace assembly that may be introduced into the vertebrae of a patient's spine during a surgical procedure by coupling a brace to a pedicle screw as a single assembly as described further in co-pending and commonly assigned U.S. patent application Ser. No. 10/690,211, filed Oct. 21, 2003, entitled "SYSTEM AND METHOD FOR STABILIZING OF INTERNAL STRUCTURES." FIG. 5 shows the installation of example stabilization device 50 with respect to vertebrae L4 and L5. Embodiments of a displacement device described herein may be used with other stabilization devices such as that of U.S. Pat. No. 6,530,929 issued to Justis et al., or in procedures that do not involve implanted stabilization devices at all.

Although an example surgical procedure will be described in further detail with respect to FIGS. 8 and 9, a brief overview of an example procedure may be helpful to put the use of a displacement device into context. A small incision may be made through the skin and a device is used to pinpoint where a pedicle screw, such as pedicle screw 602, is to be placed. Dilators, such as dilators 503 and 504, are introduced until a diameter suitable for passing the pedicle screw and its extensions is achieved. After the appropriate diameter is achieved, brace (or "rod") 601 is attached to pedicle screw ("anchor") 602 to form a brace-screw assembly. The assembly is placed at the distal end of cannula 501, inserting pedicle screw 602 into a pre-tapped hole in vertebrae L4. Then, pedicle screw ("anchor") 603 is inserted through cannula 502 into a pre-tapped hole in vertebrae L5. Once these screws are in place, dilators 503, 504 are removed, and a tool is used to part the muscle bundle below the skin between vertebrae L4 and L5. The muscles and other tissue are only separated to a point where brace 601 may pass. Thus, the procedure may be performed with minimal invasion because no incision is needed between the small incisions by which cannulas 501, 502 may pass.

After separating the muscles, brace 601 is positioned by pivoting brace 601 into position as shown by the arrow pointing downward in FIG. 5. Again, this procedure will be discussed in further detail later with respect to FIGS. 8 and 9. However, FIG. 5 shows how brace 601 may be positioned between pedicle screws 602 and 603. Once brace 601 has been positioned in the area between pedicle screws 602, 603, the surgeon may assess what angular and lateral adjustments may be made in the vertebrae L4 and L5, and accordingly, the surgeon may use the displacement device as described with respect to FIGS. 1-4 in order to make these adjustments before locking brace 601 into place. While brace 601 is used for stabilization in this example device, in other devices other types of elements may be used such as a flexible material or a wire. A cage, autograft or any other type of interbody fusion device may be placed in between the vertebrae bodies. The device could be used with a dynamic stabilization device.

Figure 6:
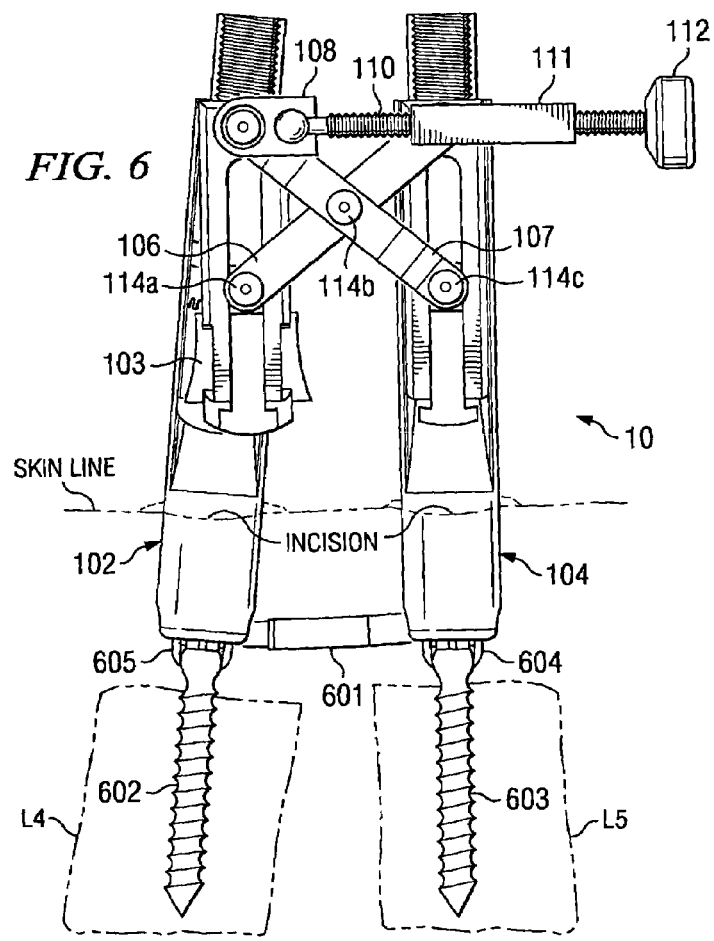
FIG. 6 shows an example of the assembled displacement device of FIG. 2 when in use with the example stabilization device of FIG. 5.

FIG. 6 illustrates the example displacement device 10 in use with the example stabilization device 50 of FIG. 5. The guide tubes 102 and 104 of displacement device 10 are placed over anchor extensions 606 and 607. Anchor extensions 606 and 607 are removably attached to rod cages 605 and 604 respectively. Guides 102 and 104 may be displaced relative to each other responsive to manipulation of the user interface (knob 112 in this example).

As shown in FIG. 6, when knob 112 is turned, cross-action members 106 and 107 move which displaces guide tubes 102 and 104 relative to one another. Depending on whether compression or distraction of L4 and L5 is desired, guides 102 and 104 will either be placed in closer relative position to each other (by compression) or be pushed apart (by distraction).

In an embodiment of the present invention, guide tubes 102 and 104 may be used to perform adjustments to the relative displacement of L4 and L5 after brace 601 is inserted between pedicle screws 602, 603 but before it is locked down to such pedicle screws using locking caps. The pedicle screws can be moved relative to each other by displacement device 10, wherein rod cages 605, 604 are rotated and have angular motion to the heads of the pedicle screws 602, 603. In an alternative embodiment, the pedicle screws may be locked into position prior to insertion of locking caps. In this scenario, displacement device 10 may force a particular angulation on the pedicle screws 602, 603 even when the pedicle screws have been locked into position. In either case, a displacement technique, such as compression or distraction, may be performed. For example, while doing a fusion, the surgeon may first perform distraction in order to insert an interbody device. Later the surgeon may compress the vertebrae to embed the interbody device and secure the stabilization device (with set screws) before stitching the incisions made for each of the cannulas.

When in use in the example procedure of FIG. 6, the majority of the displacement device 10 would not be positioned inside the patient's body. Rather, the skin line typically would be just below the sloped portion 119, 120 of guide tubes 102, 104 respectively as shown in FIG. 6. Because most of the displacement device is located outside the patient's body, smaller incisions may be used because the incisions would only need to be as wide as guide tubes 102 and 104. Thus, no incision would be needed for insertion of cross-action members 106, 107 or threaded rod 110, for example, because no additional incisions are needed over those required for inserting the anchors. This is useful both for the patient and for the surgeon. The patient benefits because smaller incisions are made due to the smaller size of the inserted position of the displacement device, resulting in a potentially faster recovery time. The surgeon also benefits because he/she may perform distraction and subsequently perform compression without having to remove the device from its placement in the patient or without having to switch devices to perform each type of displacement. Further, the portion of the device that the surgeon operates is positioned far enough above the incision line that it is easy for the surgeon to turn knob 112 making it user-friendly to perform the desired displacement technique.

Figure 7:
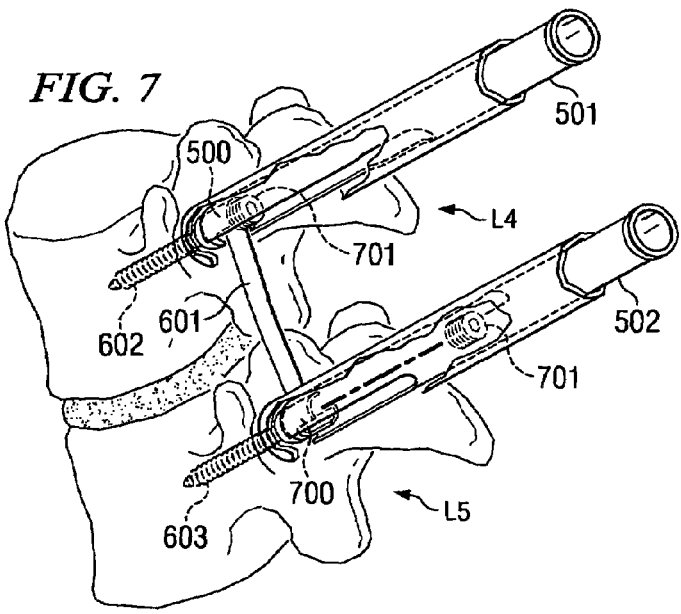
FIG. 7 shows a cut-away view illustrating a stage of stabilizing/fixing the relative position of bony structures with the example stabilization device.

After the desired displacement of L4 and L5 relative to each other is made, FIG. 7 shows a cut-away view illustrating a stage of stabilizing/fixing the displaced position of L4 and L5 bony structures with the example implanted stabilization device 50. Set screws 701, or other locking devices, are introduced down cannulas 501 and 502 to lock each end of brace 601 to its respective pedicle screw 602, 603, while displacement device 10 (not shown in FIG. 7) maintains the desired displacement of L4 and L5. Once the set screws are locked down, the displacement device 10 can be removed. The resulting implanted stabilization device 50 is shown in FIG. 9.

Figure 8:
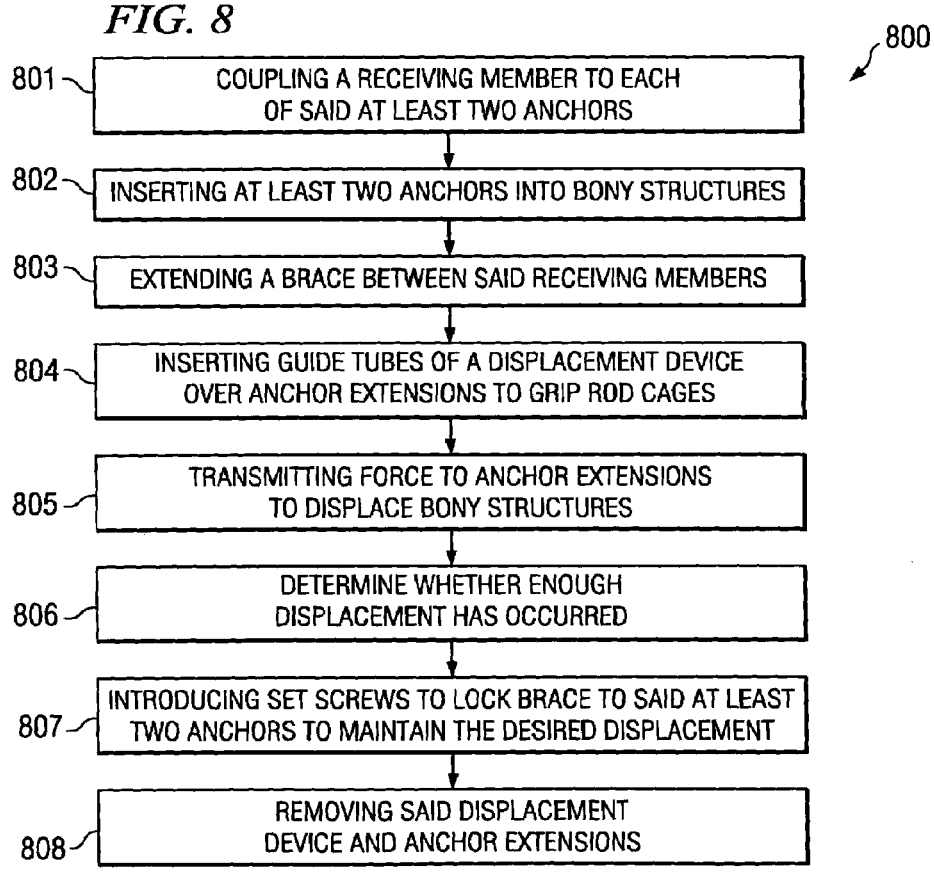
FIG. 8 shows an operational flow diagram displacing bony structures relative to each other in accordance with certain embodiments.
Figure 9:
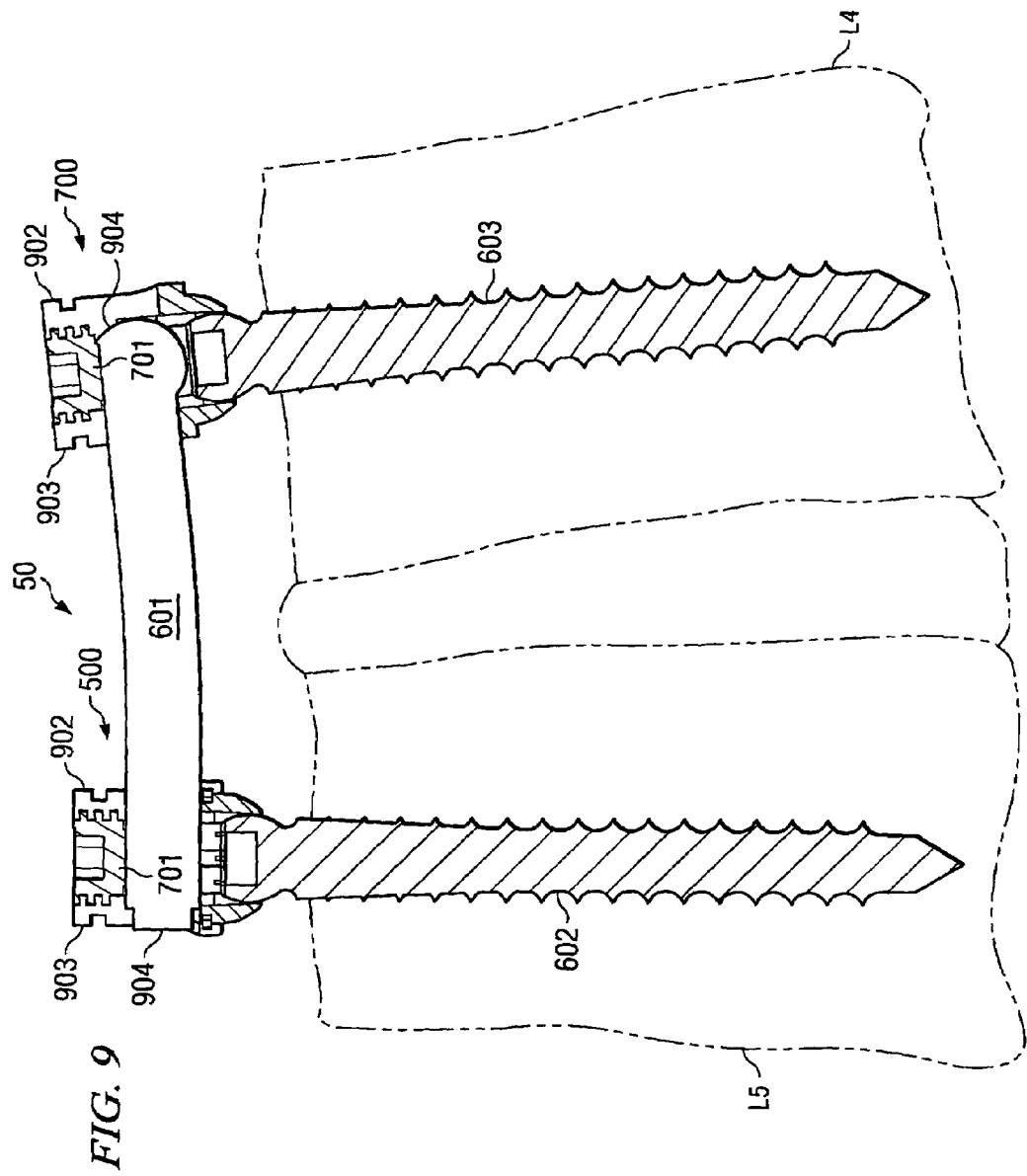
FIG. 9 shows the example stabilization device resulting from the stabilization stage of FIG. 7 in accordance with one embodiment.

Turning to FIG. 8, a flow diagram for operation of a displacement device during a spinal procedure according to one embodiment of the invention is shown. The flow diagram of FIG. 8 will be discussed with reference to the device 50 described above. The resulting implanted stabilization device 50 is shown in FIG. 9. Assemblies 500 and 700 (FIG. 9) are coupled to pedicle screws 602 and 603, respectively in process 801. The pedicle screws are assembled with the extensions and rod cages prior to insertion into the vertebrae bodies. In process 802, pedicle screws 602 and 603 are inserted into vertebrae of a patient's spine, such as vertebrae L4 and L5, respectively. Such assemblies 500 and 700 each form a receiving member for receiving closure member (e.g., set screw) 701. Generally, such receiving member formed by assemblies 500 and 700 is a noncontiguous (e.g., open-back member) having at least two walls, such as walls 902 and 903, that are separated by slots. As described further herein, closure member 701 and walls 902 and 903 are formed to have complementary threads that are formed in an interlocking manner that preferably aids in preventing splaying of the receiving members. In process 803, brace 601 is extended from assembly 500 to assembly 700.

In implanting such stabilization device 50, in accordance with one embodiment, a surgeon identifies the desired vertebral levels and pedicle positions via standard techniques. Once the target vertebrae (vertebra levels L4 and L5 in this example) are identified, a small incision is made through the patient's skin and a tracking needle (or other device) is inserted to pinpoint exactly where each screw is to be placed. A fluoroscope, or other x-ray technique, is used to properly position the tracking needle. Once the proper position is located, a first guide wire (K wire) is positioned with its distal end against the pedicle of vertebrae L4, and a second guide wire (K wire) is positioned with its distal end against the pedicle of vertebrae L5. The surgeon then slides a series of continuing larger sized dilators down each of these guide wires.

Approximately four or five dilators are used until a diameter suitable for passing the pedicle screw and its extensions is achieved. A tap is sent down over the K wire to tap a hole into the pedicle in preparation for receiving the anchor, which in this case is a pedicle screw. This tap will usually be a size slightly smaller than the pedicle screw thread size selected for that patient and that level.

After the hole is tapped and the K wire and the inner dilators are removed, the surgeon is ready to introduce the anchor (e.g., pedicle screw) into the vertebrae. Prior to inserting the screw, brace 601 is attached to screw 602 to form a brace-screw assembly. This assembly then is positioned at the distal end of a first cannula and a screwdriver or wrench is inserted into the first cannula and attached to the proximal end of brace 601, and the entire assembly then is inserted into a remaining dilator. The screwdriver engages with proximal end 904 of brace 601 so as to allow the surgeon to screw pedicle screw 602 into the pre-tapped hole in vertebrae L5. Pressure on the screwdriver forces the screw to be in-line with the brace, which, in turn, is in-line with the screwdriver.

This same procedure may be repeated for each additional level, in this case L4, except that screw 603 has assembly 700 affixed thereto. Assembly 700 is adapted to receive the proximal end 904 of brace 601 as is more fully described below.

Once both screws 602 and 603 are in place in vertebrae L4 and L5, respectively, the remaining dilator is removed, and the surgeon slides a blunt dissection tool into the skin incision and gently parts the muscle bundle below the skin between vertebrae L4 and L5. Alternatively, the blunt dissection tool could go down the second cannula (through which screw 603 was inserted) and, starting at the bottom of the second cannula, work open the muscle bundle between the cannula working upward as far as is necessary. Using this procedure, the muscles (and other tissue) only need to be separated to a point where the brace 601 must pass. Thus, the separation need not go to the skin level. This reduces patient trauma even further.

Once an opening in the muscles has been developed between the first and second cannulas, brace 601 then is positioned, by pivoting (as described above with respect to FIG. 5) and sliding a tool down the first cannula in which it resides to engage the proximal end 904 of brace 601.

Then, angular and lateral adjustments may be made using a displacement device. As discussed above, displacement may include compression, distraction, or a combination of distraction and compression. In order to perform displacement, guide tubes of a displacement device are inserted over anchor extensions in process 804. Although the displacement device is inserted over the anchor extensions in the example embodiment, further embodiments provide for additional devices to be inserted over the bone anchor for direct compression and/or distraction. Another embodiment has the displacement device placed over extensions or bone anchors, such as a device for applying force in a direction that is perpendicular to the direction in which distraction or compression occurs, as in a spondylolisthesis reduction. Force is then transmitted to the anchor extensions in order to begin compression or distraction in process 805. Alternatively, force is transmitted directly to the rod cages in order to begin compression or distraction. The surgeon may engage the displacement mechanism by turning knob 112, as discussed above with respect to FIG. 1.

Assuming that distraction is desired, then the surgeon may choose to place an interbody device into the patient and distract while the device is being inserted. Alternatively, the surgeon may choose to perform distraction before the interbody device is introduced into the patient's body. Following introduction of the interbody device, then compression may be performed in order to ensure that the device is properly positioned relative to the bony structures.

In a further embodiment, in order to determine when the desired amount of compression or distraction has been achieved, the surgeon may use as force measurement mechanism or displacement scale device as described with respect to FIG. 8.

A device then may be used in process 806 to determine if enough compression or distraction has been performed such as a device that will measure how much threaded block 111 has moved relative to threaded rod coupling 108. This device 301 (shown in FIG. 3) will employ a basic scaling technique where the display of the device may be set at zero, and the device will count incrementally based on the number of turns that knob 112 completes. This typically would be based on a scale where one turn of knob 112 translates into 1 millimeter of advancement, although another scale may be used as desired. The surgeon may view the display of device 301 and determine whether further displacement is desired.

In another embodiment, the level of compression or distraction may be measured using a force measurement device 302 (as shown in FIG. 2). This device preferably is located inside threaded block 111, and the device may include a stationary member and a member that may be deflected depending on the amount of force that is created by compression or distraction. Again, the device 302 may have a display located on the outside of threaded block 111 for the surgeon to view to determine how much force has been exerted.

Although the FIGURES have been described with respect to a device that performs both compression and distraction with minimal invasion, alternative embodiments may provide a device that performs compression alone or distraction alone while resulting in minimal invasion of the patient. As an example, assume there is a device to perform compression alone. Although the device may be constructed to perform both compression and distraction, the device may be configured so that when the device is loosened following compression, the cross-members disengage and no force is exerted in the opposite direction. Alternatively, the device may be configured to perform distraction.

After all angular and lateral adjustments are made, set screws 901 are introduced down the first and second cannulas to lock each end of brace 601 to its respective anchor to maintain the desired displacement in process 807. Once the proximal end 904 of brace 601 is snapped in place to screw 602 and set screws 901 are tightened, the displacement device and anchor extensions may be removed and the incision closed in process 808. The process of using such a stabilization device 50 in which a brace-screw assembly (of brace 601 attached to pedicle screw 602) are first inserted via a first cannula and attached to a vertebrae (e.g., vertebrae L5) and then brace 601 is pivoted such that one end 904 remains positioned over pedicle screw 602 and its opposite end is positioned over pedicle screw 603 is described further in the '211 patent application.

FIGS. 10a and 10b show alternative embodiments of the present invention where the user interface described with respect to FIG. 1 has been replaced with a set of handles that may be configured to perform compression or distraction. Although the user interface has been altered, the cross-action mechanism and guide tubes as described in FIG. 1 remain the same and are numbered in FIGS. 10a and 10b according to their placement in FIG. 1.

Turning to FIG. 10a, this figure illustrates an example embodiment of a user interface employing handles that are manipulated to result in compression. The handle assembly includes upper handle 1001 and lower handle 1004, which are interconnected at a center attachment 1003. Upper handle 1001 is joined to lever 1002 which is positioned in a first position 1007 or a second position 1008 depending on whether compression or distraction is desired. The first position 1007 is used to produce the distraction of the guides. The second position 1008 is used to produce compression of the guides. When the user squeezes the handle assembly when the lever 1002 is in second position 1008 (as shown by the arrow pointing downward on upper handle 1001), weight is applied to member 1005 to cause a downward shift and causing pivot 1006 to rotate clockwise as shown by the arrow on pivot 1006, causing guide tubes 102, 104 to move closer together (as shown by the arrow pointing downward to the right of guide tube 104).

Similarly, FIG. 10b shows an example embodiment of a user interface employing handles that are manipulated to result in distraction. Again, upper handle 1001 is joined to lever 1002, but in this case, lever 1002 is positioned in first position 1007 in the slot provided in member 1005. When the user squeezes the handle assembly, depressing upper handle 1001 (as shown by the arrow pointing downward on upper handle 1001), force is applied to pivot 1006, wherein pivot 1006 rotates counter-clockwise (as shown by the arrow on pivot 1006), causing guide tubes 102, 104 to be move apart (as shown by the arrow pointing upward below guide tube 104).

Although user interfaces employing a threaded rod mechanism or a set of handles for manipulating a displacement mechanism have been described, other means for displacement include, but are not limited to, CAM, rack and pinion as well as a circular linear motion device.

Figure 11:
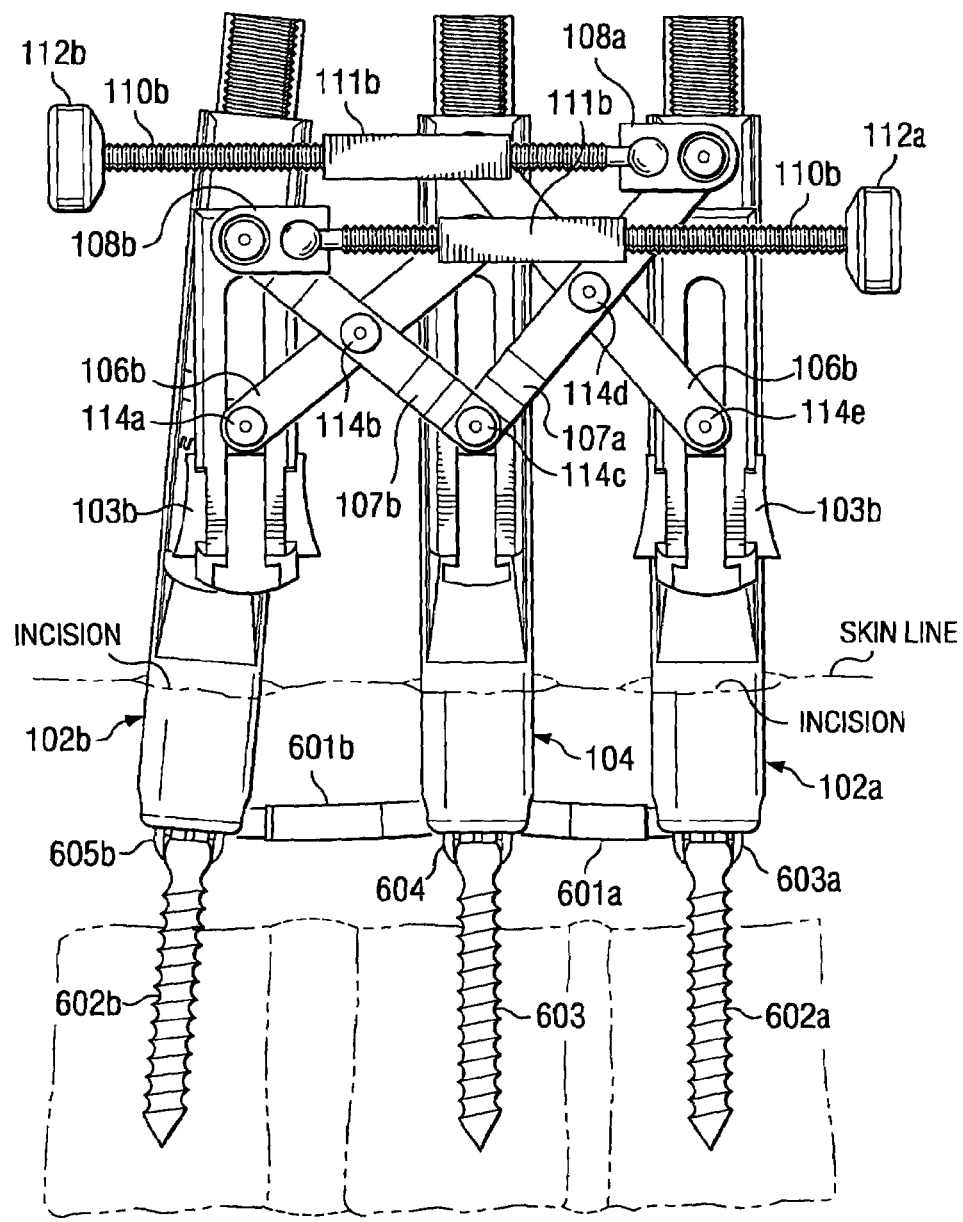
FIG. 11 shows an example displacement device configured for multi-level surgery.

FIG. 11 illustrates an example displacement device having more than two guide tubes. Guide tubes 102B and 104 are depicted as described above with respect to FIG. 6. Guide tubes 102B and 104 may be displaced relative to each other responsive to manipulation of the user interface (knob 112B in this example). When knob 112B is turned, cross-action members 106B and 107B move which displaces guide tubes 102B and 104 relative to one another, depending on whether compression or distraction is desired. Guide tube 104 is stationary and guide tube 102B moves relative to guide tube 104. Similarly, guide tubes 102A and 104 may be displaced relative to each other responsive to manipulation of the user interface (knob 112A in this example). When knob 112A is turned, cross-action members 106A and 107A move which displaces guide tubes 102A and 104 relative to each other. Again, guide tube 104 is stationary and guide tube 102A moves relative to guide tube 104. Accordingly, the displacement device shown makes it possible to displace more than two vertebrae (such as L3, L4, and L5) relative to each other. Although FIG. 11 depicts a displacement device having three guide tubes affixed to three anchors, further embodiments provide for additional guide tubes to be included in the displacement device.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A surgical instrument for adjusting distances between bony structures, said surgical instrument comprising:

a first elongated member having a proximal end, a distal end, and a longitudinal axis running from said proximal end to said distal end of said first elongated member, wherein said first elongated member has a first through-hole extending from said proximal end of said first elongated member to said distal end of said first elongated member, and said distal end of said elongated member is adapted to couple with a first vertebra via a first bone engaging member, a second elongated member having a proximal end, a distal end, and a longitudinal axis running from said proximal end to said distal end of said second elongated member, wherein said second elongated member has a second through-hole extending from said proximal end of said second elongated member and to said distal end of said second elongated member, and said distal end of said elongated member is adapted to couple with a second vertebra via a second bone engaging member, an engaging element having a proximal end, a distal end and a longitudinal axis, wherein said engaging element is pivotably coupled to said second elongated member, a length adjuster for moving said first elongated member and said second elongated member toward or away from one another, a first member and a second member, each of said first and second members coupled to said first elongated member and said engaging element such that said longitudinal axis of said first elongated member and said longitudinal axis of said engaging element is maintained in a general parallel relationship, and an angular adjuster coupled to said second elongated member and said engaging element so as to allow adjustment of an angle of said longitudinal axis of said first elongated member relative to said longitudinal axis of said second elongated member.

2. The surgical instrument of claim 1 further comprising a user interface coupled to said length adjuster.

3. The surgical instrument of claim 2 wherein said user interface includes a knob.

4. The surgical instrument of claim 1 wherein said length adjuster is a threaded rod.

5. The surgical instrument of claim 4 wherein said threaded rod comprises a left-hand thread.

6. The surgical instrument of claim 5 wherein when said threaded rod is turned clockwise, a distance between said first and second elongated elements increases.

7. The surgical instrument of claim 6 wherein when said threaded rod is turned counter-clockwise, a distance between said first and second elongated elements decreases.

8. The surgical instrument of claim 4 wherein said threaded rod comprises a right-hand thread.

9. The surgical instrument of claim 8 wherein when said threaded rod is turned clockwise, a distance between said first and second elongated elements decreases.

10. The surgical instrument of claim 9 wherein when said threaded rod is turned counter-clockwise, a distance between said first and second elongated elements increases.

11. The surgical instrument of claim 1 wherein said first member is pivotably coupled to said second member.

12. The surgical instrument of claim 1 wherein a first end of said first member is slidably coupled to said first elongated member and a second end of said first member is rotatably coupled to said engaging element.

13. The surgical instrument of claim 12 wherein a first end of said second member is slidably coupled to said engaging element and a second end of said second member is rotatably coupled to said first elongated member.

14. The surgical instrument of claim 1 wherein said first elongated member includes a first longitudinal channel and said engaging element includes a second longitudinal channel, wherein said first longitudinal channel and said second longitudinal channel are in a general parallel relationship.

15. The surgical instrument of claim 14 further comprising a first slider element and a second slider element, wherein said first slider element is slidingly coupled to said first longitudinal channel and said second slider element is slidingly coupled to said second longitudinal channel.

16. The surgical instrument of claim 15 wherein said first member has a distal end and a proximal end and said second member has a distal end and a proximal end, wherein said proximal end of said first member is pivotably coupled to said first elongated member and said proximal end of said second member is pivotally pivotably coupled to said engaging element.

17. The surgical instrument of claim 16 wherein said distal end of said first member is pivotally pivotably coupled to said second slider element and said distal end of said second member is pivotably coupled to said second slider element.

18. The surgical instrument of claim 16 wherein said first member is pivotably coupled to said second member.

19. A surgical instrument for adjusting distances between bony structures, said surgical instrument comprising:
a first elongated member having a proximal end, a distal end, and a longitudinal axis running from said proximal end to said distal end of said first elongated member, wherein said distal end of said elongated member is adapted to couple with a first vertebra via a first bone engaging member,
a second elongated member having a proximal end, a distal end, and a longitudinal axis running from said proximal end to said distal end of said second elongated member, wherein said distal end of said elongated member is adapted to couple with a second vertebra via a second bone engaging member,
an engaging element having a longitudinal axis, wherein said engaging element is pivotably coupled to said second elongated member,
a length-adjusting mechanism coupled to said first elongated member and said second elongated member,
a parallel aligner coupled to said first elongated member and said engaging element such that said longitudinal axis of said first elongated member and said longitudinal axis of said engaging element is maintained in a general parallel relationship,
an angular adjusting mechanism coupled to said second elongated member and said engaging member such that an angle between said longitudinal axis of said first elongated member is adjustable relative to said longitudinal axis of said second elongated member,
wherein said angular adjusting mechanism includes a thumb slide,
wherein said second elongated member includes a first set of teeth and said thumb slide includes a second set of teeth.

20. The surgical instrument of claim 19 wherein said thumb slide is spring-biased so that said second set of teeth interlocks with said first set of teeth.

21. The surgical instrument of claim 20 wherein when said thumb slide is pressed, said spring bias is overcome and said second set of teeth is not interlocked with said first set of teeth.

22. A surgical instrument for adjusting distances between bony structures, said surgical instrument comprising:
a first guide tube having a first proximal end and a first distal end and a first longitudinal axis running from said proximal end to said distal end and a first through-hole extending from said first proximal end to said first distal end;
a second guide tube, having a second proximal end and a second distal end and a second longitudinal axis running from said proximal end to said distal end and a second through-hole extending from said second proximal end to said second distal end;
a first arm coupled to said first guide tube,
an engaging element coupled to said second guide tube;
a user interface comprising a threaded rod for adjusting a lateral distance between said first arm and said engaging member, in a lateral direction of motion;
wherein a reference plane is defined as a plane containing said second longitudinal axis of said second guide tube, together with said lateral direction of motion provided by said threaded rod;
an angular adjustment means for adjusting an angular position between said first guide tube and said engaging element, said angular position being measured with respect to rotation around an axis that is perpendicular to said reference plane; and
an angular fixation means for angularly locking said first guide tube relative to said engaging element.

23. A surgical instrument for adjusting distances between bony structures, the surgical instrument comprising:
a first guide tube and a second guide tube;
a first and second longitudinal guide means, wherein the first longitudinal guide means is coupled to the first guide tube and the second longitudinal guide means is coupled to the second guide tube;
a lateral adjustment means for adjusting a lateral distance between the first and second longitudinal guide means;
an angular adjustment means for adjusting an angular position between the first guide tube and the first longitudinal guide means; and
an angular fixation means for angularly locking the first guide tube relative to the first longitudinal guide means,
further comprising:
a third guide tube;
a third longitudinal guide means, wherein the third longitudinal guide means is coupled to the third guide tube;
a second lateral adjustment means for adjusting the relative lateral distance between the third and second longitudinal guide means;
a second angular adjustment means for adjusting an angular position between the third guide tube and the third longitudinal guide means; and
an angular fixation means for angularly locking the third guide tube relative to the third longitudinal guide means.

24. A surgical instrument for adjusting distances between bony structures, said surgical instrument comprising:
- a first guide tube having a first proximal end and a first distal end and a first longitudinal axis running from said proximal end to said distal end and a first through-hole extending from said first proximal end to said first distal end;
- a second guide tube, having a second proximal end and a second distal end and a second longitudinal axis running from said proximal end to said distal end and a second through-hole extending from said second proximal end to said second distal end;
- a first arm coupled to said first guide tube;
- an engaging element coupled to said second guide tube;
- a user interface comprising a set of handles having a lever that may be selectively engaged in a slot having a first position and a second position to perform either compression or distraction when said handles are manipulated by a user, said user interface for adjusting a lateral distance between said first arm and said engaging member, in a lateral direction of motion;
- wherein a reference plane is defined as a plane containing said second longitudinal axis of said second guide tube, together with said lateral direction of motion;
- an angular adjustment means for adjusting an angular position between said first guide tube and said engaging element, said angular position being measured with respect to rotation around an axis that is perpendicular to said operative plane; and
- an angular fixation means for angularly locking said first guide tube relative to said engaging element.

25. The surgical instrument of claim 24 wherein compression occurs when force is applied to shift said lever to said second position of said slot that is closer to said lateral adjustment means.

26. The surgical instrument of claim 25 wherein distraction occurs when a force is applied to shift said lever to said first position of said slot that is farther from said lateral adjustment means.

27. A surgical instrument for adjusting distances between bony structures, said surgical instrument comprising:
- a first elongated member having a proximal end, a distal end, and a longitudinal axis running from said proximal end to said distal end of said first elongated member, wherein said distal end of said elongated member is adapted to couple with a first vertebra via a first bone engaging member;
- a second elongated member having a proximal end, a distal end, and a longitudinal axis running from said proximal end to said distal end of said second elongated member, wherein said distal end of said elongated member is adapted to couple with a second vertebra via a second bone engaging member;
- an engaging element having a proximal end, a distal end and a longitudinal axis, wherein said engaging element is pivotably coupled to said second elongated member near said proximal end of said second elongated member, wherein in a first position, said second elongated member and said engaging element are generally parallel to said first elongated member, and in a second position, said second elongated member is not parallel to said first elongated member and said engaging element is generally parallel to said first elongated member;
- a length adjuster for causing relative motion between said first elongated member and said second elongated member in a direction substantially perpendicular to one of said longitudinal axes of one of said elongated members; and
- an angular adjuster coupled to said second elongated member and said engaging element.

28. A surgical instrument for adjusting distances between bony structures, said surgical instrument comprising:
- a first elongated member having a proximal end, a distal end, and a longitudinal axis running from said proximal end to said distal end of said first elongated member, wherein said distal end of said elongated member is adapted to couple with a first vertebra via a first bone engaging member,
- a second elongated member having a proximal end, a distal end, and a longitudinal axis running from said proximal end to said distal end of said second elongated member, wherein said distal end of said elongated member is adapted to couple with a second vertebra via a second bone engaging member,
- an engaging element having a proximal end, a distal end and a longitudinal axis, wherein said engaging element is pivotably coupled to said second elongated member,
- a length adjuster for causing linear displacement between said first elongated member and said second elongated member; and
- a first member and a second member, each of said first and second members coupled to said first elongated member and said engaging element such that said longitudinal axis of said first elongated member and said longitudinal axis of said engaging element is maintained in a general parallel relationship, and
- an angular adjuster coupled to said second elongated member and said engaging member so as to allow adjustment of an angle of said longitudinal axis of said second elongated member relative to said longitudinal axis of said first elongated member.

* * * * *